(12) United States Patent
Ishii et al.

(10) Patent No.: US 9,220,799 B2
(45) Date of Patent: Dec. 29, 2015

(54) BACTERICIDAL AGENT COMPOSITION

(71) Applicants: SUNSTAR ENGINEERING INC., Osaka (JP); SUNSTAR INCORPORATED, Osaka (JP); NATIONAL UNIVERSITY CORPORATION OKAYAMA UNIVERSITY, Okayama (JP)

(72) Inventors: Miwa Ishii, Osaka (JP); Toru Oka, Osaka (JP); Yoshimitsu Nakayama, Osaka (JP); Masumi Torii, Osaka (JP); Masaru Sugimori, Osaka (JP); Shogo Takashiba, Okayama (JP); Hiroshi Maeda, Okayama (JP); Fumi Mineshiba, Okayama (JP); Kimito Hirai, Okayama (JP)

(73) Assignees: SUNSTAR ENGINEERING INC., Osaka (JP); NATIONAL UNIVERSITY CORPORATION OKAYAMA UNIVERSITY, Okayama (JP); SUNSTAR INC., Osaka (JP)

(*) Notice: Subject to any disclaimer, the term of this patent is extended or adjusted under 35 U.S.C. 154(b) by 0 days.

(21) Appl. No.: 14/708,631

(22) Filed: May 11, 2015

(65) Prior Publication Data
US 2015/0258232 A1 Sep. 17, 2015

Related U.S. Application Data

(62) Division of application No. 14/377,315, filed as application No. PCT/JP2013/054475 on Feb. 22, 2013.

(30) Foreign Application Priority Data

Feb. 29, 2012 (JP) ................................ 2012-043932

(51) Int. Cl.
| | |
|---|---|
| *A01N 25/00* | (2006.01) |
| *A61K 31/00* | (2006.01) |
| *A01N 65/00* | (2009.01) |
| *A61K 9/14* | (2006.01) |
| *A61L 2/18* | (2006.01) |
| *A01N 25/34* | (2006.01) |
| *A01N 59/12* | (2006.01) |
| *A01N 65/08* | (2009.01) |
| *A01N 25/02* | (2006.01) |
| *A01N 43/36* | (2006.01) |

(52) U.S. Cl.
CPC ................... *A61L 2/18* (2013.01); *A01N 25/00* (2013.01); *A01N 25/02* (2013.01); *A01N 25/34* (2013.01); *A01N 43/36* (2013.01); *A01N 59/12* (2013.01); *A01N 65/08* (2013.01)

(58) Field of Classification Search
None
See application file for complete search history.

(56) References Cited

U.S. PATENT DOCUMENTS

| 6,638,978 B1 | 10/2003 | Kabara |
| 2007/0205161 A1 | 9/2007 | Chiba et al. |
| 2010/0151043 A1 | 6/2010 | Mano et al. |
| 2012/0128749 A1 | 5/2012 | Tsuji et al. |

FOREIGN PATENT DOCUMENTS

| JP | 62-269673 | 11/1987 | |
| JP | 9-278610 | 10/1997 | |
| JP | 2003-528820 | 9/2003 | |
| JP | 2005-246293 | 9/2005 | |
| JP | 2006-69909 | 3/2006 | |
| JP | 2006-182663 | 7/2006 | |
| JP | 2006-312588 | 11/2006 | |
| JP | 2007-137791 | 6/2007 | |
| JP | 2010-5130 | 1/2010 | |
| JP | WO 2011/111600 A1 * | 9/2011 | ......... B01D 11/0211 |
| JP | 2011-213689 | 10/2011 | |
| JP | 2013-10758 | 1/2013 | |
| WO | 01/43549 | 6/2001 | |
| WO | 2008/072371 | 6/2008 | |
| WO | 2011/016529 | 2/2011 | |

OTHER PUBLICATIONS

Machine Translation of WO 2011/111600 A1 (Sep. 2011).*
International Search Report issued Apr. 16, 2013 in International (PCT) Application No. PCT/JP2013/054475.

* cited by examiner

*Primary Examiner* — Jeffrey T Palenik
(74) *Attorney, Agent, or Firm* — Wenderoth, Lind & Ponack, L.L.P.

(57) ABSTRACT

[Problem] To provide: a bactericidal agent composition which can exhibit an excellent bactericidal effect in the presence of an organic substance and against biofilms; a method for producing the bactericidal agent composition; and a sterilization method using the bactericidal agent composition. [Solution] A bactericidal agent composition which comprises water containing ultrafine bubbles having a most frequent particle diameter of 500 nm or less and a bactericidal component. Preferably, the density of most frequent particles of the ultrafine bubbles are 10,000 particles or more and the density of ultrafine bubbles each having a particle diameter of 1000 nm or less is 1,000,000 particles or more.

4 Claims, 2 Drawing Sheets

BACTERICIDAL AGENT COMPOSITION

TECHNICAL FIELD

The present invention relates to a novel bactericidal agent composition capable of sterilizing in the presence of various kinds of organic contaminations in the environment or sterilizing bacteria in biofilms by means of using water containing ultrafine bubbles, a method for producing the bactericidal agent composition, and a sterilization method using the bactericidal agent composition.

BACKGROUND ART

Bactericidal agents are used extensively in all areas such as engineering, cosmetics, food processing, pharmaceuticals, agriculture, and dairy husbandry. The types of bactericidal agents are quite versatile and examples used in medical and food fields include chlorine sterilizers, iodine sterilizers, peroxide sterilizers, aldehyde sterilizers, phenolic sterilizers, biguanide sterilizers, mercury sterilizers, alcoholic sterilizers, quaternary ammonium salt sterilizers, and amphoteric surfactant sterilizers.

However, most of these sterilizers suffer considerable drop in bactericidal power in the face of contaminating by organic substances such as proteins or in the presence of biofilms covered with polysaccharides or proteins. This leads to a discrepancy between bactericidal evaluation in the laboratory and on-site evaluation and the resulting failure to inhibit bacterial growth and eventually causes infection. Particularly notable in this respect are biofilms which can sometimes pose serious problems both in the living environment of humans and in the industry. Take, for example, a dwelling environment; biofilms can be a cause of discomfort if they produce slimes, clogging or malodor in toilets, kitchens, bathrooms, etc. Another potential cause of infections is the bacteria in biofilms formed in water-circulating bathtubs in hot spa facilities and the like. Problems are also encountered in industrial fields, as exemplified by corrosion from biofilms that are formed on the inner surfaces of sewage pipes and on ship bottoms; biofilms on production lines in plants can be another cause of microbial contamination. In medical-related areas, biofilms formed in tubes for dialysis and other applications, as well as in medical devices such as endoscopes and contact lenses can be a source of infection; diseases can also be caused by biofilm formation in skin and other human tissues. In the human oral cavity, it is well known that biofilms formed on teeth which are commonly called "dental plaques" can cause dental caries and periodontal disease. In food-related areas, biofilms formed on perishable goods such as vegetables, as well as materials for processed foods and cooking utensils are potential causes of putrefaction and food poisoning. These problems are currently coped by specifying bactericidal concentrations for actual use that are much higher than those found in the laboratory.

It was proposed that penetrability into biofilms be improved by methods characterized by additional use of anionic surfactants (Patent Documents 1, 2 and 3). These known techniques, however, had their own problems. For example, in actual use, contaminating by organic substances is assumed and bactericidal concentrations are specified that are much higher than those found in the laboratory; however, even such higher concentrations were unable to kill the bacteria found in excessive contaminations or biofilms and, what is more, they were undesirable from the viewpoints of human body and environmental safety. Another problem was that fatty acid esters of glycerol which would not lose bactericidal or antibacterial activity in the contamination by organic substances had no antibacterial activity against Gram-negative bacteria (Non-Patent Document 1). To deal with this problem, it was proposed that ethylenediaminetetraacetic acid, a chelatant having bactericidal power against Gram-negative bacteria, be additionally used to make up for the disadvantage of fatty acid esters of glycerol (Patent Documents 4, 5 and 6); however, ethylenediaminetetraacetic acid had a problem with the latitude of formulation in that only limited combinations of formulations was permitted, as exemplified by the case where it reacted with hypochlorous acid or salts thereof and the available chlorine concentration decreased to result in a lower bactericidal power. As already mentioned, it was proposed that penetrability into biofilms be improved by methods characterized by additional use of anionic surfactants (Patent Documents 1, 2 and 3) but they also had a problem with the latitude of formulation, as exemplified by the attenuation of bactericidal power due to an electrical interaction that occurred when they were used in combination with cationic sterilizers.

PRIOR ART LITERATURE

Patent Literature

Patent Document 1: JP 2006-69909A
Patent Document 2: JP 2006-182663A
Patent Document 3: JP 2006-312588A
Patent Document 4: JP 1997-278610 A
Patent Document 5: JP2003-528820 A
Patent Document 6: JP1987-269673 A

Non-Patent Literature

Non-Patent Document 1: Koshohin Bofu/Sakkinzai no Kagaku (Japanese translation of "Cosmetic and Drug Preservation: Principles and Practice"), ed. by John J. Kabara, translated by Koichi Yoshimura & Hirofumi Takigawa, published by Fragrance Journal Ltd. on Apr. 10, 1990, pp. 249-263

SUMMARY OF INVENTION

Problem to be Solved by the Invention

The present invention has as its objectives providing a bactericidal agent composition which can exhibit an excellent bactericidal effect in the presence of an organic substance and against biofilms, a method for producing the bactericidal agent composition, and a sterilization method using the bactericidal agent composition.

Means for Solving the Problem

In one aspect, the present invention relates to a bactericidal agent composition which comprises ultrafine bubbles having a most frequent particle diameter of 500 nm or less and a bactericidal component. In a preferred mode, the "density of most frequent particles" among the ultrafine bubbles which is the number per milliliter (mL) of particles having the most frequent particle diameter is $1 \times 10^4$ particles or more. In another preferred mode, the "total particle density" which is the total number of ultrafine bubbles per mL is $1 \times 10^6$ or more. In addition, the density of ultrafine bubbles each having a particle diameter of 1000 nm or less which is the number per mL of ultrafine bubbles having a particle diameter of 1000 nm or less is preferably $1 \times 10^6$ particles or more.

The interior of the above-described ultrafine bubbles may be filled with one or more gases selected from among air, oxygen, hydrogen, nitrogen, carbon dioxide, argon, neon, xenon, fluorinated gases, ozone, and inert gases.

In addition, the bactericidal component which is used in the present invention may be an iodine bactericidal component, a peroxide bactericidal component, an aldehyde bactericidal component, a phenolic bactericidal component, a biguanide bactericidal component, a mercury bactericidal component, an alcoholic bactericidal component, a quaternary ammonium salt bactericidal component, an amphoteric surfactant bactericidal component, and a naturally derived bactericidal component.

In another aspect, the present invention provides a method for producing a bactericidal agent composition which comprises mixing water containing ultrafine bubbles having a most frequent particle diameter of 500 nm or less with a bactericidal component. The present invention also provides a method for producing a bactericidal agent composition which comprises generating ultrafine bubbles having a most frequent particle diameter of 500 nm or less within water containing a bactericidal component. In a preferred mode, the density of most frequent particles among the ultrafine bubbles are $1 \times 10^4$ particles or more, with $1 \times 10^5$ particles or more being further preferred. In another preferred mode, the total fine particle density and the density of ultrafine bubbles each having a particle diameter of 1000 nm or less are each $1 \times 10^6$ particles or more.

In a further aspect, the present invention provides a sterilization method using the bactericidal agent composition according to its first aspect; in particular, it provides a sterilization method comprising a step in which the bactericidal agent composition according to its first aspect is brought into contact with a biofilm.

As used herein, the term "biofilm" refers to higher structure entities formed by microorganisms and may be exemplified by films formed through binding with extracellular polymeric substances (EPS) such as polysaccharides. More specific examples of biofilms include those which were already mentioned above, i.e., biofilms formed in residential toilets, kitchens and bathrooms, biofilms formed in water-circulating bath tubs as in hot spa facilities, biofilms formed in various kinds of piping such as sewage pipes, biofilms formed on ship bottoms, biofilms formed on production lines in plants, biofilms formed in tubes for dialysis and other applications, biofilms formed in medical devices such as endoscopes and contact lenses, biofilms formed on the skin or in the oral cavity of human body, biofilms formed on perishable goods such as vegetables and materials for processed foods, and biofilms formed on cooking utensils.

Effects of the Invention

According to the present invention, there are provided a bactericidal agent composition which can exhibit an excellent bactericidal effect in the presence of an organic substance and against biofilms, and a sterilization method using the same.

MODES FOR CARRYING OUT THE INVENTION

The ultrafine bubbles to be used in the present invention have a most frequent particle diameter of 500 nm or less, preferably a most frequent particle diameter of 300 nm or less, more preferably a most frequent particle diameter of 150 nm or less, and most preferably a most frequent particle diameter of 110 nm or less; the density of most frequent particles is preferably $1 \times 10^4$ particles or more, more preferably $5 \times 10^4$ particles or more, even more preferably $5 \times 10^5$ particles or more, still more preferably $5 \times 10^6$ particles or more, yet more preferably $1 \times 10^7$ particles or more, still even more preferably $5 \times 10^7$ particles or more, yet more preferably $1 \times 10^8$ particles or more, even more preferably $5 \times 10^8$ particles or more, and most preferably $7 \times 10^8$ particles or more.

In another preferred mode, the density of ultrafine bubbles having a particle diameter of 1000 nm or less and the total particle density are each preferably $1 \times 10^6$ particles or more, more preferably $4 \times 10^6$ particles or more, even more preferably $4 \times 10^7$ particles or more, still more preferably $1 \times 10^8$ particles or more, yet more preferably $4 \times 10^8$ particles or more, still even more preferably $1 \times 10^9$ particles or more, yet more preferably $3 \times 10^9$ particles or more, even more preferably $5 \times 10^9$ particles or more, still more preferably $7 \times 10^9$ particles or more, yet more preferably $1 \times 10^{10}$ particles or more, even more preferably $2 \times 10^{10}$ particles or more, and most preferably $4 \times 10^{10}$ particles or more. In a still more preferred mode, bubbles larger than 1000 nm are seldom found. In this case, the "total particle density" is synonymous with the density of ultrafine bubbles having a particle diameter of 1000 nm or less. In the Examples to be described later, bubbles larger than 1000 nm are seldom found, so the two terms are used as synonyms.

The particle diameter of the ultrafine bubbles to be used in the present invention is so small that it cannot be measured correctly with an ordinary particle size distribution analyzer. Hence, hereinafter, numerical values are employed that were obtained by measurements with the nanoparticle size analyzing system NanoSight Series (product of NanoSight Ltd.) The nanoparticle size analyzing system NanoSight Series (product of NanoSight Ltd.) measures the velocity of nanoparticles moving under Brownian motion and calculates the diameters of the particles from the measured velocity. A most frequent particle diameter can be verified from the size distribution of the particles present and refers to the particle diameter at which the number of particles assumes a maximum value.

Water to be used in the present invention can be selected from, but is not limited to, tap water, purified water, ion-exchanged water, pure water, ultrapure water, deionized water, distilled water, buffer solutions, clean water, natural water, filtered water, highly pure water, potable water, and electrolyzed water.

Water-soluble solvents such as alcohols, glycols, glycerol, ethers, ketones, and esters may also be added.

The zeta potential on the surfaces of ultrafine bubbles affects the stability of the bubbles. The surfaces of the ultrafine bubbles used in the present invention are electrically charged to produce a zeta potential of 5 mV or higher, preferably 7 mV or higher, more preferably 10 mV or higher, even more preferably 20 mV or higher, still more preferably 25 mV or higher, and most preferably 30 mV or higher, in absolute value.

The ultrafine bubbles to be used in the present invention can be generated by any known means, such as the use of a static mixer, the use of a venturi tube, cavitation, vapor condensation, sonication, swirl formation, dissolution under pressure, or fine pore formation. A preferred method of bubble generation is by forming a gas-liquid mixture and shearing it.

An advantageous apparatus for generating ultrafine bubbles by the gas-liquid mix and shear method is disclosed in Japanese Patent No. 4118939. In this apparatus, the greater part of a gas-liquid mixture in fluid form introduced into a fluid swirling compartment does not simply flow toward the discharge port as in the apparatus described in the prior art section but it first flows forming a swirl in the direction away from the discharge port. The swirl reaching the first end-wall member turns around and flows back toward the second end-wall member; since the returning swirl has a smaller radius of rotation than the swirl flowing toward the first end-wall member, it flows at a higher velocity, creating a sufficient shear force on the gas within the liquid to promote the formation of finer bubbles.

An aqueous solution of the bactericidal component may be treated with a suitable apparatus to generate ultrafine bubbles in it, whereby the composition of the present invention can be produced that has the bactericidal component dissolved in the water. Alternatively, the composition of the present invention can be produced by dissolving the bactericidal component in water containing ultrafine bubbles. The aforementioned water containing ultrafine bubbles may have the most frequent particle diameter and density that have been specified above.

If the bactericidal component is hydrophobic, it may be dispersed in water containing ultrafine bubbles. In this case, ultrafine bubbles may be generated in a dispersion having the bactericidal component dispersed in water. Alternatively, the bactericidal component may be added to water containing ultrafine bubbles and then dispersed in the water. As used herein, the expression of "comprising the bactericidal component" embraces two cases, one where the bactericidal component is dissolved in water and one where it is dispersed in water.

The bactericidal component to be used in the present invention may be a chlorine bactericidal component, an iodine bactericidal component, a peroxide bactericidal component, an aldehyde bactericidal component, a phenolic bactericidal component, a biguanide bactericidal component, a mercury bactericidal component, an alcoholic bactericidal component, a quaternary ammonium salt bactericidal component, an amphoteric surfactant bactericidal component, or a naturally derived bactericidal component.

Examples of the chlorine bactericidal component include sodium hypochlorite, chlorine, chloroisocyanuric acid, etc.

Examples of the iodine bactericidal component include iodine, povidone iodine, nonoxynol iodine, phenoxy iodine, etc.

Examples of the peroxide bactericidal component include hydrogen peroxide, potassium permanganate, ozone, strongly acidic water, etc.

Examples of the aldehyde bactericidal component include glutaraldehyde, phtharal, formaldehyde, etc.

Examples of the phenolic bactericidal component include isopropylmethylphenol, thymol, eugenol, triclosan, cresol, phenol, chlorocresol, parachlorometacresol, parachlorometaxylenol, ortho phenylphenol, alkyl esters of paraoxybenzoic acid, resorcin, hexachlorophene, salicylic acid, salts thereof, etc.

Examples of the biguanide bactericidal component include chlorhexidine, chlorhexidine gluconate, chlorhexidine hydrochloride, etc.

Examples of the mercury bactericidal component include mercurochrome, mercury (II) chloride, thimerosal, etc.

The alcoholic bactericidal component may be exemplified by ethanol, isopropanol, etc.

Examples of the quaternary ammonium salt bactericidal component include cetylpyridinium chloride, benzethonium chloride, benzalkonium chloride, dequalinium chloride, etc.

Examples of the amphoteric surfactant bactericidal component include N-alkyldiaminoethylglycines (e.g. N-lauryldiaminoethylglycine and N-myristyldiethylglycine), N-alkyl-N-carboxymethylammonium betaine, 2-alkyl-1-hydroxyethyl imidazoline betaine sodium, etc.

The bactericidal component to be used in the present invention may also be the naturally derived bactericidal component described below.

Examples of the naturally derived bactericidal component include: plant derived materials such as Hinokitiol, anethole, anise oil, borneol, camphor, carvone, *cassia* oil, Chenopodiaceae oil, cineol, citral, citronellal, eugenol, pinene, geraniol, lemon oil, linalol, menthol, orange oil, saflol, thymol, etc.; animal derived materials such as chitin and chitosan prepared from the shells of crustaceans, and fired seashell powders obtained by firing the shells of scallops and oysters; microbial materials such as polylysine; and enzymatic materials such as lysozyme. Antibacterial peptides that organisms produce in order to defend themselves against external microorganisms may also be used and they include, for example, histatin, defensins, lactoferrin, lactoferricin which is a decomposition product of lactoferrin, magainin, cecropin, melititin, etc. Since these peptides are innately produced by organisms, they have extremely small side effect or inhibitory actions on the living body. In addition, it would be expected that by simply cleaning the body with water containing the ultrafine bubbles, the bactericidal effect of the antibacterial peptides on the surface of the skin is so much enhanced that adequate bactericidal effects can be obtained without using additional bactericidal agents.

Antibacterial plant extracts can also be used as the naturally derived antibacterial component. Specific examples include: grapefruit seed extract, as well as plant extracts from; *Kochia scoparia*, etc. of the family Chenopodiaceae; *Belamcanda chinensis*, etc. of the family Iridaceae; *Hypericum perforatum* of the family Hypericaceae; *Boswellia carterii* Birdw, *Cedronella canariensis*, etc. of the family Burseraceae; *Adenophora triphylla* var. *japonica*, etc, of the family Campanulaceae; *Echinacea purpurea, Matricaria recutita* (or *Anthemis nobilis*), *Arctium lappa* L., *Solidago canadensis* var. *scabra* (or *Solidago altissima*), *Atractylodes lancea*, etc. of the family Asteraceae (or Compositae); *Coptis japonica* (Thunb.) Makino, etc. of the family Ranunculaceae; *Lonicera japonica*, etc. of the family Caprifoliaceae; *Laurus nobilis Laurus*, etc. of the family Lauraceae; *Humulus lupulus*, etc. of the family Moraceae; *Scutellaria baicalensis, Oregano Origanum vulgare, Schizonepeta tenuifolia, Salvia officinalis*, thyme, *Melissa officinalis* Linn., *Mosla japonica*, lavender *Rosmarinus officinalis* L., etc. of the family Lamiaceae; *Hedychium coronarium* Koen, *Zingiber officinale*, etc. of the family Zingiberaceae; *Sambucus nigra* L., etc. of the family Caprifoliaceae; *Cryptomeria japonica*, etc. of the family Taxodiaceae; *Angelica dahurica, Saposhnikovia divaricata*, etc. the family Apiaceae; *Polygonum aviculare*, etc. of the family Polygonaceae; *Arctostaphylos uva-ursi*, etc. of the family Ericaceae; *Houttuynia cordata*, etc. of the family Saururaceae; *Tribulus terrestris*, etc. of the family Zygophyllaceae; *Cayratia japonica*, etc. of family Vitaceae; *Pimenta dioica, Melaleuca alternifolia, Eucalyptus globules, Syzygium aromaticum* (L.) Merrill & Perry, etc. of the family Myrtaceae; *Maackia amurensis, Styphnolobium japonicum, Sophora flavescens, Dalbergia cochinchinensis, Cassia siamea*, etc. of the family Fabaceae (or Leguminosae); *Liquidambar formosana* of the family Hamamelidaceae; *Phellodendron amurense*, Citrus unshiu, etc. of the family Rutaceae; *Symphytum offcinale*, etc. of the family Boraginaceae; *Berberis vulgaris* L., *Nandina domestica Nandina*, etc. of the family Berberidaceae; *Magnolia obovata* of the family Magnoliaceae; *Sanguisorba officinalis* L., rose, etc. of the family Rosaceae; *Viscum album* subsp. *coloratum*, etc. of the family Viscaceae; *Anemarrhena asphodeloides, Aspidistra elatior* Blume, *Glycyrrhiza* L., etc. of the family Liliaceae; *Gentiana macrophylla*, etc. of the family Gentianaceae; *Phyllostachys heterocycla* f. *pubescens*, etc. of the family Poaceae.

Preferred examples of the bactericidal component that may be used in the present invention include an iodine bactericidal component such as povidone iodine, a biguanide bactericidal component such as chlorhexidine gluconate, a quaternary ammonium salt bactericidal component such as benzalkonium chloride, and a plant extract such as grapefruit seed extract.

The amount of the bactericidal component to be used varies with its kind, use, etc. While the preferred amount can be determined appropriately by experiment, the bactericidal component can generally be used in amounts ranging from 10 to 0.00001 wt % of the bactericidal agent composition.

In addition to the bactericidal component described above, any optional component that is appropriate for a specific dosage form of the bactericidal agent composition of the present invention may be incorporated in it on the condition that the effects of the present invention will not be impaired; examples of such optional component are a wetting agent, a thickening agent, a stabilizer, a pH modifier, an antiseptic, a sweetener, a fragrance, a surfactant, an active ingredient, a colorant, a chelating agent, a UV absorber, a bleaching agent, an antifoaming agent, an enzyme, etc. A further improvement in the bactericidal effect can be expected by incorporating an auxiliary agent as a potentiator. If povidone iodine is used as the bactericidal component, a component that enhances its stability at low concentration may also be incorporated (JP 1993-43891A).

As the wetting agent, sugar alcohols and polyhydric alcohols such as butylene glycol, ethylene glycol, xylit, maltit, and lactit may be used in addition to the above-described component (B).

Exemplary thickening agents include cellulosic binders (e.g. carboxymethylcellulose sodium, hydroxyethyl cellulose, hydroxypropyl cellulose, hydroxypropylmethyl cellulose, hydroxymethylethyl cellulose, and methyl cellulose), xanthan gum, carrageenan, guar gum, sodium alginate, cationized cellulose, montmorillonite, gelatin, sodium polyacrylate, etc.

Exemplary pH modifiers include phthalic acid, phosphoric acid, citric acid, succinic acid, acetic acid, fumaric acid, malic acid, and carbonic acid, as well as salts thereof with potassium, sodium, and ammonium; ribonucleic acid and salts thereof; sodium hydroxide, etc.

Exemplary antiseptics include benzoates such as sodium benzoate, alkyldiaminoethylglycine hydrochloride, potassium sorbate, etc.

Exemplary sweeteners include saccharin sodium, aspartame, stevioside, *Stevia rebaudiana* extract, para-methoxycinnamic aldehyde, neohesperidin dihydrochalcone, perillartin, etc.

Exemplary fragrances include: natural fragrances such as *eucalyptus* oil, wintergreen oil, *cassia* oil, clove oil, thyme oil, sage oil, basil oil, cardamom oil, coriander oil, spearmint oil, orange oil, lemon oil, mandarin oil, lime oil, grapefruit oil, yuzu oil, sweetie (orobranco) oil, lavender oil, rosemary oil, laurel oil, chamomile oil, caraway oil, marjoram oil, celery oil, bay oil, *origanum* oil, pine needle oil, neroli oil, lemon grass oil, rose oil, jasmine oil, patchouli oil, iris concrete, rose absolute, orange flower absolute, vanilla absolute, mango absolute, patchouli absolute, ginger oleoresin, pepper oleoresin, *capsicum* oleoresin, and *Capsicum annuum* Linne extract; fragrances prepared by processing the above-mentioned natural fragrances (as by cutting the initial or last run, fractionation, liquid-liquid extraction, rendering into an essence, or rendering a powdered fragrance); isolated fragrances such as limonene, pinene, butanol, isoamyl alcohol, n-hexenol, cis-3-hexenol, cis-6-nonenol, linalol, α-terpineol, benzyl alcohol, phenylethyl alcohol, anethole, thymol, methyl chavicol, eugenol, carvone, menthone, pulegone, 1,8-cineole, ionone, calone, n-hexanal, trans-2-hexenal, citral, cinnamaldehyde, benzaldehyde, ethyl acetate, ethyl butyrate, isoamyl acetate, hexyl acetate, ethyl-2-methyl butyrate, allyl hexanoate, allyl cyclohexane propionate, linalyl acetate, menthyl acetate, menthyl lactate, carbil acetate, phenoxyethyl isobutyrate, methyl jasmonate, methyl salicylate, ethyl salicylate, methyl cinnamate, methyl anthranilate, phenylethyl glycidate, ethyl lactate, vanillin, maltol, gamma- and delta-lactone having 4-12 carbon atoms, ambrettolide, dimethyl sulfide, trimethylpyrazine, ethyl-β-methyl propionate, furaneol, ethyl cyclopentenolone, cyclotene, 2-methylbutyric acid, propionic acid, p-methoxycinnamic aldehyde, 3-1-menthoxypropane-1,2-diol, menthone glycerin acetal, spilanthol, monomenthyl succinate, linalol oxide, vanillyl butyl ether, isopulegol, etc.; compound fragrances such as strawberry flavor, apple flavor, melon flavor, banana flavor, peach flavor, raspberry flavor, pineapple flavor, grape flavor, tropical fruit flavor, mango flavor, *Prunus mume* flavor, orange flavor, lemon flavor, grapefruit flavor, tea flavor, butter flavor, milk flavor, etc.; and fragrance solvents such as ethyl alcohol, propylene glycol, triacetin, fatty acid esters of glycerol, etc.

Exemplary surfactants include nonionic surfactants, anionic surfactants, cationic surfactants, and amphoteric surfactants. Anionic surfactants include, for example, sodium alkyl sulfates such as sodium lauryl sulfate and sodium myristyl sulfate; acyl sarcosine salts such as sodium lauryl sarcosinate and sodium myristyl sarcosinate; sodium dodecylbenzenesulfonate, sodium hydrogenated coconut fatty acid monoglyceride monosulfate, and sodium lauryl sulfoacetate; N-acylglutamates such as N-acyl glutamates and sodium N-palmitoyl glutamate; as well as sodium salt of N-methyl-N-acyl taurine, sodium salt of N-methyl-N-acyl alanine, and sodium α-olefin sulfonate. Amphoteric surfactants that can be incorporated are lauryl dimethylaminoacetic acid betaine, N-palm oil fatty acid acyl-N-carboxymethyl-N-hydroxyethyl imidazolinium betaine, etc.

Exemplary pigments include Blue No. 1, Green No. 3, Yellow No. 4, Red No. 105, etc.

Examples of the auxiliary agent as a bactericidal potentiator include anionic surfactants, nonionic surfactants, amphoteric surfactants, cationic surfactants, and sugar alcohols that enhance the penetration into biofilms; an exemplary anionic surfactant is sodium lauryl sulfate, and exemplary sugar alcohols include erythritol, xylitol, sorbitol, etc.

Exemplary cationic surfactants include: alkyl trimethyl ammonium salts such as stearyl trimethyl ammonium chloride and lauryl trimethyl ammonium chloride, alkyl pyridinium salts such as cetylpyridinium chloride, dialkyl dimethyl ammonioum salts such as distearyl dimethyl ammonium chloride, poly(N,N'-dimethyl-3,5-methylenepiperidinium chloride), alkyl quaternary ammonium salts, alkyl dimethyl benzyl ammonium salts, alkyl isoquinolinium salts; dialkyl morpholinium salts, POE-alkyl amines, alkyl amine salts, polyamine fatty acid derivatives; POE-amine fatty acid derivatives; polyamine fatty acid derivatives, amyl alcohol fatty acid derivatives, benzalkonium chloride, and benzethonium chloride.

Examples of the nonionic surfactant include polyoxyethylene alkyl ethers, polyoxyethylene polyoxypropylene alkyl ethers, polyoxyethylene alkylphenyl ethers, polyglycerol esters of fatty acids, sugar esters of fatty acids, fatty acid alkanolamides, alkyl amine oxides, alkyl amide amine oxides, etc.

Exemplary chelating agent include alkaline builders such as sodium tripolyphosphate, sodium metasilicate, sodium carbonate, sodium hydroxide, and potassium hydroxide, as well as ethylenediaminetetraacetate (EDTA), N-hydroxyethyl-ethylenediaminetriacetate (HEDTA), and triethanolamine.

Exemplary UV absorbers may be benzophenone-based (e.g. 2-hydroxybenzophenone and 2,4-dihydroxybenzophenone), salicylate-based (e.g. phenyl salicylate and 2,4-di-t-butylphenyl-3,5-di-t-butyl-4-hydroxybenzoate), benzotriazole-based [(2'-hydroxyphenyl)benzotriazole and (2'-hydroxy-5'-methylphenyl)benzotriazole], acrylate-based [ethyl-2-cyano-3,3-diphenyl acrylate and methyl-2-carbomethoxy-3-(paramethoxybenzyl)acrylate], and so forth.

Exemplary antifoaming agents include silicones (e.g. dimethyl polysiloxane), mineral oils (e.g. spindle oil and kerosene), and metal soaps having 12-22 carbon atoms (e.g. calcium stearate).

Exemplary enzymes include proteases, lipases, amylases, cellulases, oxidases, etc.

The above-described components are given only for illustrative purposes and any known agents can be used unless they are deleterious to the effects of the present invention. The respective components may be incorporated in any amounts and can be used to an extent that will not impair the effects of the present invention.

The foregoing description of the present invention and the description of the Examples that follow are only intended to provide a detailed explanation of various exemplary embodiments of the present invention and skilled artisans can make various improvements and changes of the embodiments disclosed herein without departing from the scope of the present invention. Therefore, the description herein will in no way limit the scope of the present invention, which shall be determined only by the recitation in the appended claims.

EXAMPLES

Preparation of Water Containing Ultrafine Bubbles

Figure 1:
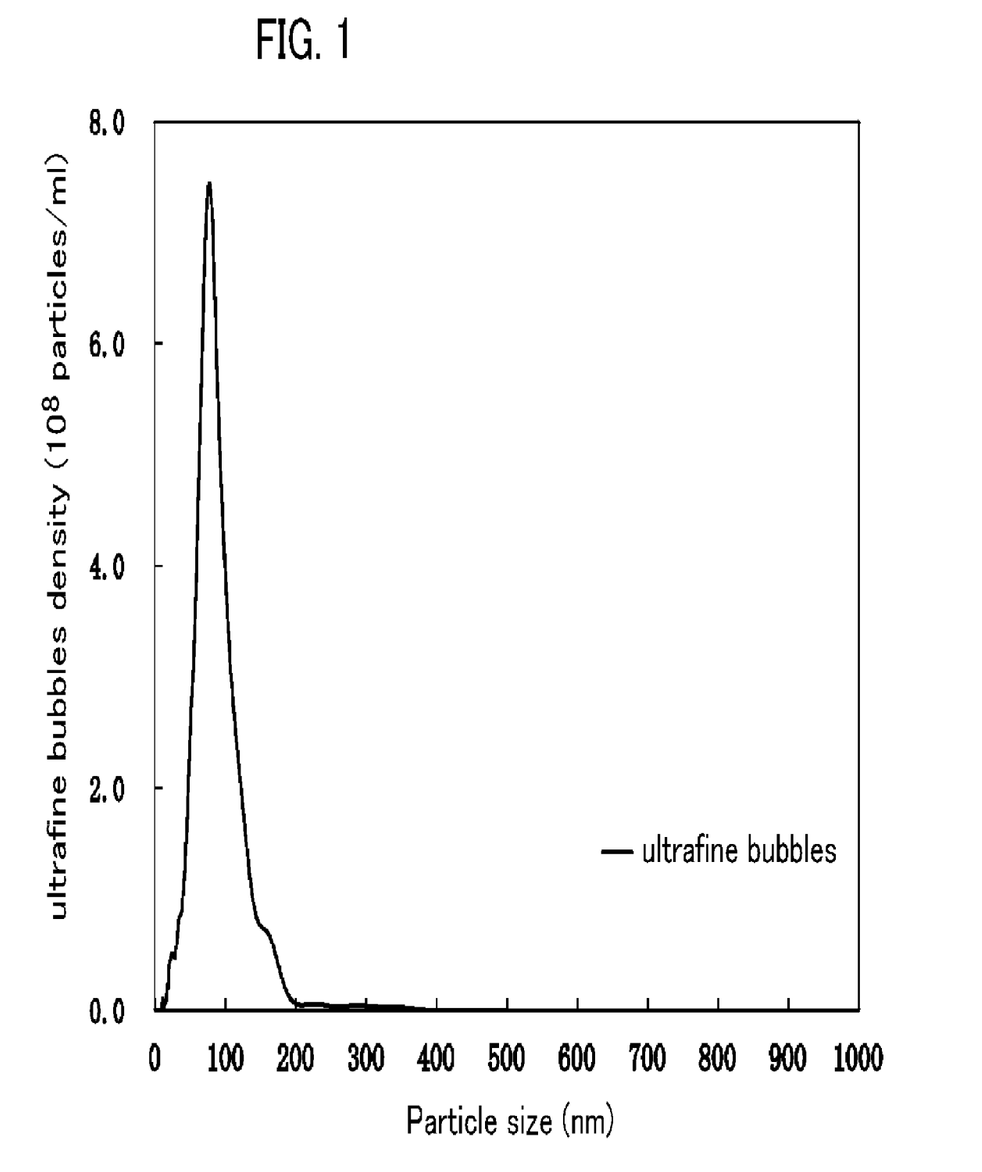
FIG. 1 is a graph showing the result of measuring the particle size distribution of bubbles in water containing ultrafine bubbles (since the apparatus's upper limit of detection was exceeded, water as the analyte was diluted with purified water and the resulting data of measurement was multiplied by the dilution ratio to provide the result shown in Fig.).
Figure 2:
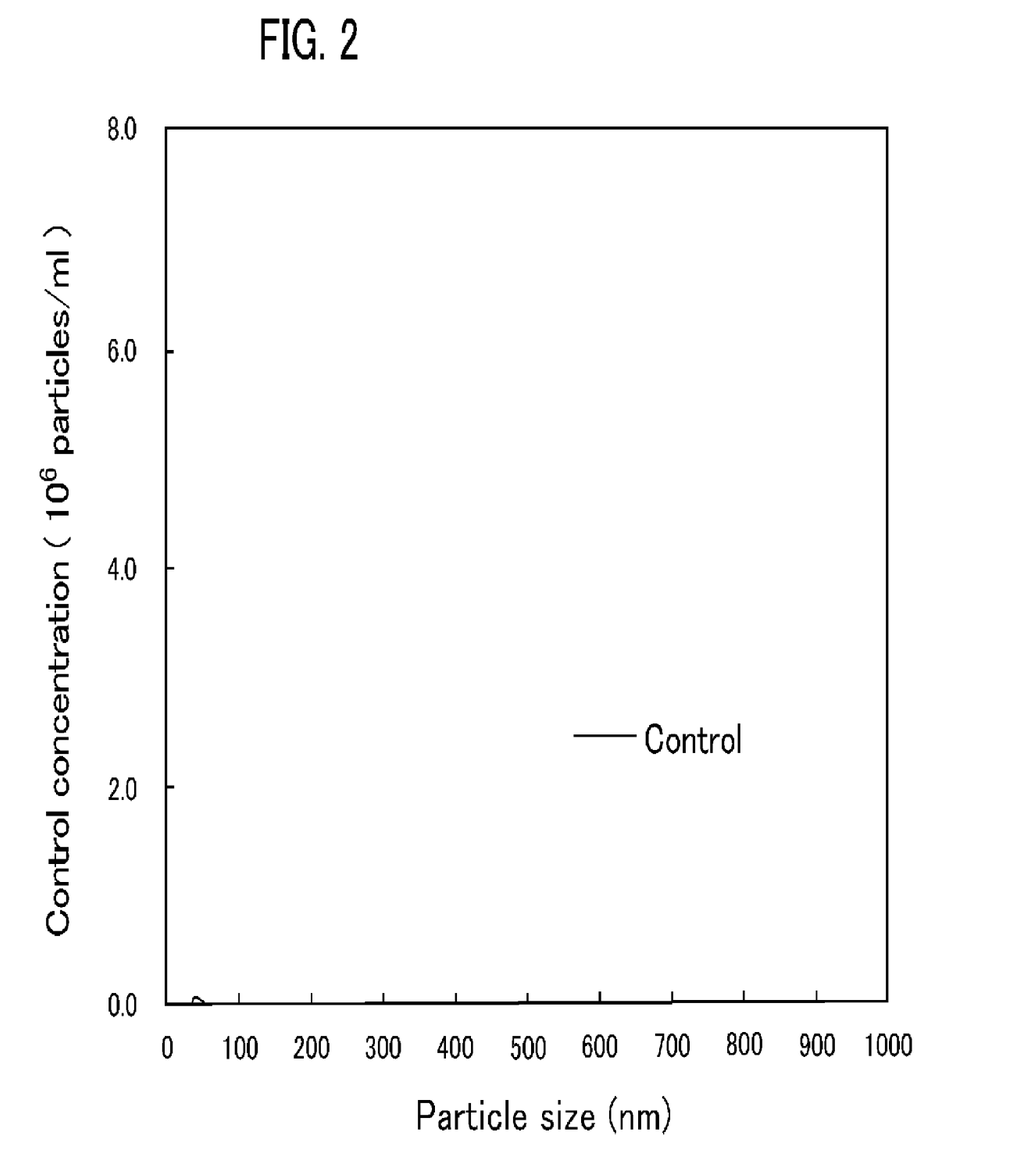
FIG. 2 is a graph showing the result of measuring the particle size distribution of bubbles in purified water as specified in the Japanese Pharmacopoeia.

Ultrafine bubbles were generated in purified water (Japanese Pharmacopoeia) using BUVITAS of KYOWA KISETSU which was a device for generating ultrafine bubbles by the gas-liquid mix and shear method. The particle diameters of the generated ultrafine bubbles were measured with the nanoparticle size analyzing system NanoSight Series (product of NanoSight Ltd.) When the apparatus's upper limit of detection was exceeded, water as the analyte was diluted with purified water and the resulting data of measurement was multiplied by the dilution ratio; the thus processed data of measurement are shown in FIG. 1. The horizontal axis of the graph in FIG. 1 represents the particle diameter in nanometers and the vertical axis represents the number of ultrafine bubbles particles per millimeter ($10^8$/mL). FIG. 2 shows the result of a measurement of fine bubbles in the purified water of the Japanese Pharmacopoeia.

The water containing the generated ultrafine bubbles had a most frequent particle diameter of 77 nm; the particle density at the most frequent particle diameter was $7.44 \times 10^8$ per milliliter and the total particle density was $4.11 \times 10^{10}$ per milliliter.

The purified water of the Japanese Pharmacopoeia had such low particle densities that the size distribution was not a normal distribution; the result of the measurement was therefore attributed to noise.

In the following Examples, water containing ultrafine bubbles were prepared by the same method as described above, and the blanks as Comparative Examples used the purified water of the Japanese Pharmacopoeia in place of the water containing ultrafine bubbles.

Example 1

Bactericidal Effect on *Pseudomonas aeruginosa* in Organic Substance

The test was conducted in accordance with AOAC Official Method 964.02 Testing Disinfectants against *Pseudomonas aeruginosa*.

1) Conditioning Test Liquids

The water prepared as described above to contain oxygen-filled ultrafine bubbles or the purified water of the Japanese Pharmacopoeia was used to dilute povidone iodine such that it was conditioned to 100 mg/L.

2) Preparing Test Bacterial Liquids

A cryopreserved bacterial strain (*Pseudomonas aeruginosa* NBRC13275) was grown in a tryptic soy agar (Difco; hereinafter referred to as TSA medium) at $36\pm1°$ C. for 18-24 hours. The grown cells were transplanted into a tryptic soy broth (Difco; hereinafter referred to as TSB medium) where they were cultured at $36\pm1°$ C. for 18-24 hours. The liquids of the thus cultured cells were conditioned with a TSB medium to an approximate value of $10^6$ CFU/mL and the resulting liquids were used as test bacterial liquids.

3) Preparing Carriers to which the Test Bacterium Adhered

A sterile bioassay cup (stainless steel Penicillin Cup 441-01 made by Sogo Rikagagu glass; hereinafter designated as a carrier) was placed in a 100-mL beaker, into which test bacterial liquids were poured in such amounts that the carrier would be completely immersed (ca. 30-40 mL). After allowing the beaker to stand for 10-15 minutes, the carrier was transferred onto a Petri dish with sterile filter paper spread on the bottom and by allowing the Petri dish to stand at $36\pm1°$ C. for $40\pm2$ minutes, the bacterial cells and the organic substance derived from the mediums were dried and adhered to the carrier.

4) Bactericidal Test

The test liquids preliminarily held at $25\pm2°$ C. were each dispensed in 10 mL into centrifugal tubes having a capacity of 50 mL; using a hook of platinum wire, the carriers to which the test bacterium adhered were put into the centrifugal tubes, one for each, and allowed to act at $25\pm2°$ C. for 20 minutes. Thereafter, the carriers were transferred into centrifugal tubes containing 10 mL of an inactivator SCDLP medium (Eiken Chemical Co., Ltd.), one for each, so as to inactivate the bactericidal component in the test liquid adhering to the carrier. The carriers were then treated with a sonicator at $20\pm2°$ C. for 5 minutes to wash off the test bacterium; the test liquids were agitated for an additional minute with a vortex mixer to prepare sample liquids for cell count and the number of surviving cells was counted. A control was prepared by the same procedure as described above, except that the test liquids were replaced by sterile physiological saline.

5) Counting Surviving Cells

The sample liquids for cell count (stock liquids) were serially diluted 10-fold with sterile physiological saline; the sample liquids or the series of dilutions, each weighing a volume of 1 mL, were transferred aseptically into Petri dishes and, after mixing with 20 mL of a TSA medium, they were solidified and cultured at $36\pm1°$ C. for 48 hours. Thereafter, colonies growing on the medium were counted to determine the number of surviving cells per carrier (lower limit for quantification: 10 CFU/carrier).

6) Results

The results are shown Table 1. To obtain those results, the test was replicated in five runs (n=5) and after eliminating minimum and maximum values, an averaged cell count for n=3 was indicated as a logarithmic value.

The control had a surviving cell count of 4.9. The povidone iodine conditioned with purified water had a value of 3.9 whereas the povidone iodine conditioned with the water containing oxygen-filled ultrafine bubbles had a value of 1.4; an obvious difference was recognized between the bactericidal efficacies of the two.

ferred into a sterilized test tube and, after adding a suitable amount of a ½ nutrient medium, the contents were agitated with the test tube agitator such that the viable cell count was adjusted to be within the range of $2.5 \times 10^8$ to $12.5 \times 10^8$ cfu/ml. After standing at the test temperature for an hour, 1.0 mL of a substance serving as a model contamination (bovine serum albumin in aqueous solution; 30 g/L) was added and mixed; the resulting mixture was left to stand for 2 minutes to prepare a test bacterial liquid.

3) Preparing Carriers to which the Test Bacterium Adhered and Performing a Bactericidal Test A stainless steel disk was prepared as described in the Test for Bacteria Eradiating Activity of Residential Synthetic Detergents and Soaps; 0.01 mL of the test bacterial liquid,

TABLE 1

| Sample description | Conditioning Water | Most frequent particle diameter (nm) | Most frequent particle density ($10^8$ particles/ml) | Total particle density ($10^{10}$ particles/ml) | Povidone iodine Concentration (mg/L) | Cell count CFU/carrier | | | | log value |
|---|---|---|---|---|---|---|---|---|---|---|
| | | | | | | n1 | n2 | n3 | average | |
| Control (physiological saline) | — | — | — | — | — | 68000 | 110000 | 62000 | 80000 | 4.9 |
| Povidone iodine | water | — | — | — | 100 | 23000 | 19000 | 26000 | 8000 | 3.9 |
| | water containing oxygen-filled ultrafine bubbles | 91 | 3.1 | 2.3 | 100 | 10 | 10 | 50 | 23 | 1.4 |

Example 2

Bactericidal Effect on *Staphylococcus aureus* subsp. *aureus* NBRC12732 in Organic Contaminations In accordance with the Test for Bacteria Eradiating Activity of Residential Synthetic Detergents and Soaps (as specified by the Detergent and Soap Fair Trade Committee), bactericidal efficacy against *Staphylococcus aureus* subsp. *aureus* NBRC12732 was investigated.

1) Conditioning of Test Liquids

Water containing nitrogen-filled ultrafine bubbles were prepared as described above.

A grapefruit seed extract as a natural antibacterial agent was diluted with the water containing ultrafine bubbles or purified water so that it was conditioned to 0.5%.

2) Preparing Test Bacterial Liquids

A sterile conical flask was charged with about 5 mL of a ½ nutrient medium acclimatized to a test temperature (25±1° C.) and a suitable quantity of sterilized glass beads; thereafter, a platinum loop of cells of an incubated test bacterium was added. The contents of the flask were agitated with a test tube agitator. Subsequently, about 1 mL of the contents were transafter being agitated again, was metered onto the disk and spread uniformly on a surface of the test piece. The disk (test piece) was lidded with a Petri dish and allowed to stand at 25±1° C. until the test bacterial liquid became apparently dry. Thereafter, 0.1 mL of the test liquid was metered and spread uniformly onto a surface of the disk. The disk was lidded with the Petri dish and allowed to stand at 25±1° C. for a minute. Thereafter, inactivation was conducted as instructed and the viable cells were counted.

4) Results

The results are shown in Table 2. To obtain those results, the test was replicated in five runs (n=5) and after eliminating minimum and maximum values, an averaged cell count for n=3 was indicated as a logarithmic value.

The natural antibacterial agent conditioned with water had a viable cell count of 4.9 whereas the natural antibacterial agent conditioned with the water containing ultrafine bubbles had a value of 2.5; an obvious difference was recognized between the bactericidal efficacies of the two.

TABLE 2

| Sample description | Conditioning Water | Most frequent particle diameter (nm) | Most frequent particle density ($10^8$ particles/ml) | Total particle density ($10^{10}$ particles/ml) | Natural antibacterial agent concentration (%) | Cellcount CFU/carrier | | | | log value |
|---|---|---|---|---|---|---|---|---|---|---|
| | | | | | | n1 | n2 | n3 | average | |
| Grapefruit seed extract | water | — | — | — | 0.5 | 1900 | 39000 | 35000 | 25000 | 4.4 |
| | water containing nitrogen-filled | 103 | 5.0 | 4.1 | 0.5 | 640 | 55 | 170 | 290 | 2.5 |

TABLE 2-continued

| Sample description | Conditioning Water | Most frequent particle diameter (nm) | Most frequent particle density ($10^8$ particles/ml) | Total particle density ($10^{10}$ particles/ml) | Natural antibacterial agent concentration (%) | Cellcount CFU/carrier | | | | log value |
|---|---|---|---|---|---|---|---|---|---|---|
| | | | | | | n1 | n2 | n3 | average | |
| | ultrafine bubbles | | | | | | | | | |

Example 3

Bactericidal Effect on Cariogenic Bacteria-Formed Biofilms

1) Conditioning Test Liquids

Either water containing oxygen-filled ultrafine bubbles prepared as described above or purified water was used to dilute povidone iodine to condition the same to 1.0 mg/mL and 10 mg/mL.

2) Preparing Test Bacterial Liquids

*Streptococcus mutans* (ATCC25175) was grown in a Tryptic soy Broth supplemented with 0.5% yeast extract (the resulting medium is hereinafter referred to as TSBY medium) at 37° C. until the $OD_{660}$ was between 0.6 and 0.8 ($10^8$ cells/mL); the product was used as a test bacterial liquid.

3) Biofilm Formation

A TSBY medium (plus 1% sucrose) placed in a test tube in a volume of 4950 μL was inoculated with 50 μL of the test bacterial liquid and was cultured at 37° C. for 18 hours to form a biofilm.

4) Bactericidal Test

From the test tube in which the biofilm was formed, the culture broth was removed by means of an aspirator and the biofilm was washed with 5 mL of an added PBS. After removing the PBS, 5 mL of the test liquid was treated for reaction as it was shaken with a shaking machine (37° C.×20 min). After the 20-min reaction, 5 mL of 0.4% (w/v) sodium thiosulfate in solution was added into the test tube so as to inactivate the bactericidal agent. Using a sonicator, the biofilm was detached from the inner surfaces of the test tube and dispersed with a vortex mixer thereby prepare a sample liquid for cell count; the number of surviving cells in the biofilm was then counted.

5) Counting the Number of Surviving Cells in the Biofilm

The sample liquids for cell count were diluted with a buffer solution; after culture in an MS agar medium (37° C.×36-48 hours), the number of colonies formed was counted to determine the number of surviving cells in the biofilms.

6) Results

The results are shown in Table 3. To obtain those results, the test was replicated in 5 runs (n=5).

At the concentrations of 1.0 mg/mL and 10 mg/mL, the povidone iodine samples that had been conditioned with the purified water had cell counts in biofilms that were equivalent to 616.6 cfu and 9.2 cfu, whereas the povidone iodine samples conditioned with the water containing ultrafine bubbles had corresponding values of 149.2 cfu and 0 cfu; an obvious difference was recognized between the bactericidal efficacies of the two.

TABLE 3

| Sample description | Conditioning Water | Most frequent particle diameter (nm) | Most frequent particle density ($10^7$ particles/ml) | Total particle density ($10^9$ particles/ml) | Povidone iodine concentration (mg/L) | Cell count CFU | | | | | |
|---|---|---|---|---|---|---|---|---|---|---|---|
| | | | | | | n1 | n2 | n3 | n4 | n5 | average |
| Povidone iodine | water | — | — | — | 1 | 612 | 439 | 1050 | 386 | 596 | 616.6 |
| | water containing oxygen-filled ultrafine bubbles | 100 | 2.0 | 1.6 | | 250 | 35 | 178 | 150 | 133 | 149.2 |
| | water | — | — | — | 10 | 9 | 22 | 13 | 0 | 2 | 9.2 |
| | water containing oxygen-filled ultrafine bubbles | 100 | 2.0 | 1.6 | | 0 | 0 | 0 | 0 | 0 | 0 |

Example 4

An experiment was conducted by the same method as in Example 1, except for the following points: water containing oxygen-filled ultrafine bubbles prepared as described above or purified water was used to dilute povidone iodine such that it was conditioned to 100 mg/L; in addition, the most frequent particle density of the water containing ultrafine bubbles were adjusted to orders of $10^4$, $10^5$, $10^6$, and $10^8$ per mL.

TABLE 4

| Sample description | Conditioning Water | Most frequent particle diameter (nm) | Most frequent particle density (particles/ml) | Total particle density (particles/ml) | Povidone iodine concentration (mg/L) | Cell count CFU/carrier | | | | Log value | Observed bactericidal efficacy |
|---|---|---|---|---|---|---|---|---|---|---|---|
| | | | | | | n1 | n2 | n3 | average | | |
| Control (physiological saline) | — | — | — | — | — | 170000 | 80000 | 87000 | 110000 | 5.0 | — |
| Povidone iodine | water | — | — | — | 100 | 46000 | 47000 | 39000 | 44000 | 4.6 | x |
| | water containing oxygen-filled ultrafine bubbles | 81 | $7.2 \times 10^4$ | $4.2 \times 10^6$ | | 5900 | 2200 | 7700 | 5300 | 3.7 | Δ |
| | water containing oxygen-filled ultrafine bubbles | 81 | $7.2 \times 10^5$ | $4.2 \times 10^7$ | | 4200 | <10 | <10 | <10 | 3.1 | ○ |
| | water containing oxygen-filled ultrafine bubbles | 81 | $7.2 \times 10^6$ | $4.2 \times 10^8$ | | <10 | <10 | <10 | <10 | <1.0 | ○ |
| | water containing oxygen-filled ultrafine bubbles | 81 | $7.2 \times 10^8$ | $4.2 \times 10^{10}$ | | <10 | <10 | <10 | <10 | <1.0 | ○ |

Example 5

An experiment was conducted by the same method as in Example 1, except that water containing atmospheric air- or $C_3F_8$-filled ultrafine bubbles prepared as described above or purified water was used to dilute povidone iodine such that it was conditioned to 100 mg/L.

The results are shown in Table 5.

TABLE 5

| Sample description | Conditioning Water | Most frequent particle diameter (nm) | Most frequent particle density ($10^8$ particles/ml) | Total particle density ($10^{10}$ particles/ml) | Povidone iodine concentration (mg/L) | Cell count CFU/carrier | | | | Log value |
|---|---|---|---|---|---|---|---|---|---|---|
| | | | | | | n1 | n2 | n3 | average | |
| Control (physiological saline) | — | — | — | — | — | 22000 | 34000 | 41999 | 32000 | 4.5 |
| Povidone iodine | water | — | — | — | 100 | 3200 | 1800 | 8600 | 4500 | 3.7 |
| | water containing atmospheric air-filled ultrafine bubbles | 75 | 5.7 | 4.6 | | 10 | 75 | <10 | 32 | 1.5 |
| | water containing $C_3F_8$-filled ultrafine bubbles | 76 | 2.7 | 1.3 | | <10 | <10 | <10 | <10 | 1.0 |

The invention claimed is:

1. A method of sterilization comprising a step in which a bactericidal agent composition comprising ultrafine bubbles having a most frequent particle diameter of 500 nm or less and a bactericidal component is brought into contact with a biofilm,
wherein the bactericidal component is selected from the group consisting of: chloroisocyanuric acid, nonoxynol iodine, phenoxy iodine, potassium permanganate, glutaraldehyde, phtharal, formaldehyde, parachlorometha-cresol, parachlorometaxylenol, ortho phenylphenol, alkyl esters of paraoxybenzoic acid, hexachlorophene, mercury (II) chloride, thimerosal, benzethonium chloride, dequalinium chloride, N-lauryldiaminoethylglycine, N-myristyldiethylglycine, N-alkyl-N-carboxymethylammonium betaine, 2-alkyl-1-hydroxyethyl imidazoline betaine sodium, Hinokitiol, cassia oil, Chenopodiaceae oil, geraniol, saflol, polylysine, lysozyme, histatin, defensins, lactoferrin and lactoferricin.

2. The method according to claim 1, wherein a density of most frequent particles among the ultrafine bubbles is $1 \times 10^4$ particles or more.

3. The method according to claim 1, wherein a density of ultrafine bubbles each having a particle diameter of 1000 nm or less is $1 \times 10^6$ or more.

4. The method according to claim 1, wherein an interior of the ultrafine bubbles is filled with one or more gases selected from the group consisting of air, oxygen, hydrogen, nitrogen, carbon dioxide, argon, neon, xenon, a fluorinated gas, ozone, and an inert gas.

* * * * *